(12) United States Patent
Schlapfer et al.

(10) Patent No.: US 6,582,436 B2
(45) Date of Patent: Jun. 24, 2003

(54) DEVICE FOR CONNECTING A LONGITUDINAL SUPPORT TO A BONE ANCHOR

(75) Inventors: Fridolin Schlapfer, Glarus (CH); Martin Hess, Holstein (CH)

(73) Assignee: Synthes (U.S.A.), Paoli, PA (US)

( * ) Notice: Subject to any disclaimer, the term of this patent is extended or adjusted under 35 U.S.C. 154(b) by 85 days.

(21) Appl. No.: 09/820,174

(22) Filed: Mar. 29, 2001

(65) Prior Publication Data

US 2001/0047173 A1 Nov. 29, 2001

Related U.S. Application Data

(63) Continuation of application No. PCT/CH98/00415, filed on Sep. 29, 1998.

(51) Int. Cl.[7] ............................................... A61B 17/84
(52) U.S. Cl. ......................................... 606/73; 606/61
(58) Field of Search ......................... 606/60, 61, 72, 606/73

(56) References Cited

U.S. PATENT DOCUMENTS

| | | | |
|---|---|---|---|
| 5,451,225 A | 9/1995 | Ross, Jr. et al. | 606/59 |
| 5,584,834 A | 12/1996 | Errico et al. | 606/61 |
| 5,752,954 A | 5/1998 | Mata et al. | 606/59 |
| 6,063,090 A | 5/2000 | Schlapfer | 606/61 |

FOREIGN PATENT DOCUMENTS

| | | |
|---|---|---|
| EP | 0 384 001 A1 | 8/1990 |
| EP | 0 524 441 B1 | 1/1993 |
| EP | 0 700 664 A1 | 3/1996 |
| WO | WO 88/01152 | 2/1988 |

Primary Examiner—David O. Reip
(74) Attorney, Agent, or Firm—Pennie & Edmonds LLP

(57) ABSTRACT

A device for connecting a longitudinal support to a bone anchor having a rounded head includes a body defining a chamber for receiving the rounded head of the bone anchor and a first channel for receiving the longitudinal support. Further, a first sleeve is slidable over the body for compressing the chamber, a second sleeve is slidable over the body for biasing the longitudinal support against the first sleeve, and a fastener is operatively associated with the body for biasing the second sleeve toward the first sleeve. The forces exerted on the second sleeve by the fastener are transferred to the first sleeve in a plane perpendicular to the central axis. Preferably, the longitudinal support contacts the first sleeve at first and second contact points or zones and one of the sleeves includes at least one extended portion for contacting the other sleeve at at least one additional contact point or zone.

31 Claims, 3 Drawing Sheets

Detail B

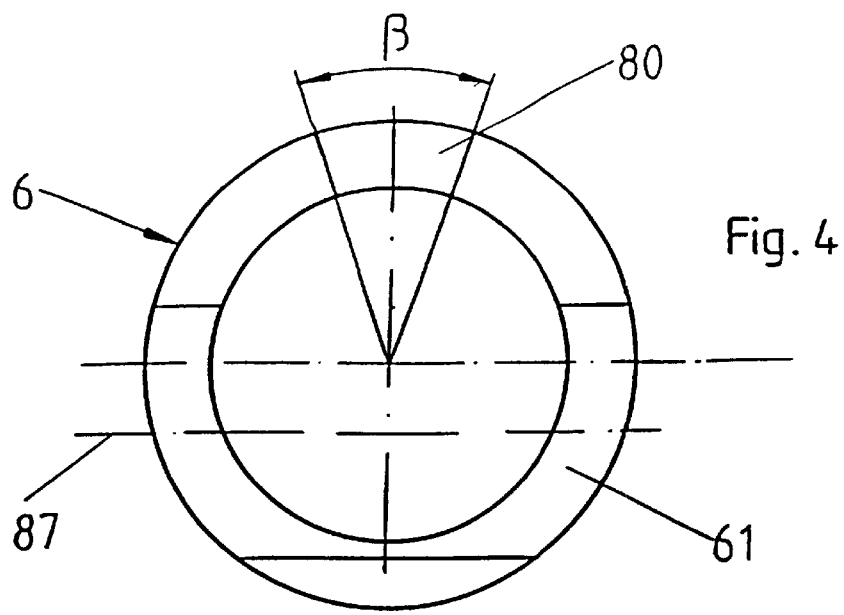
Fig. 4
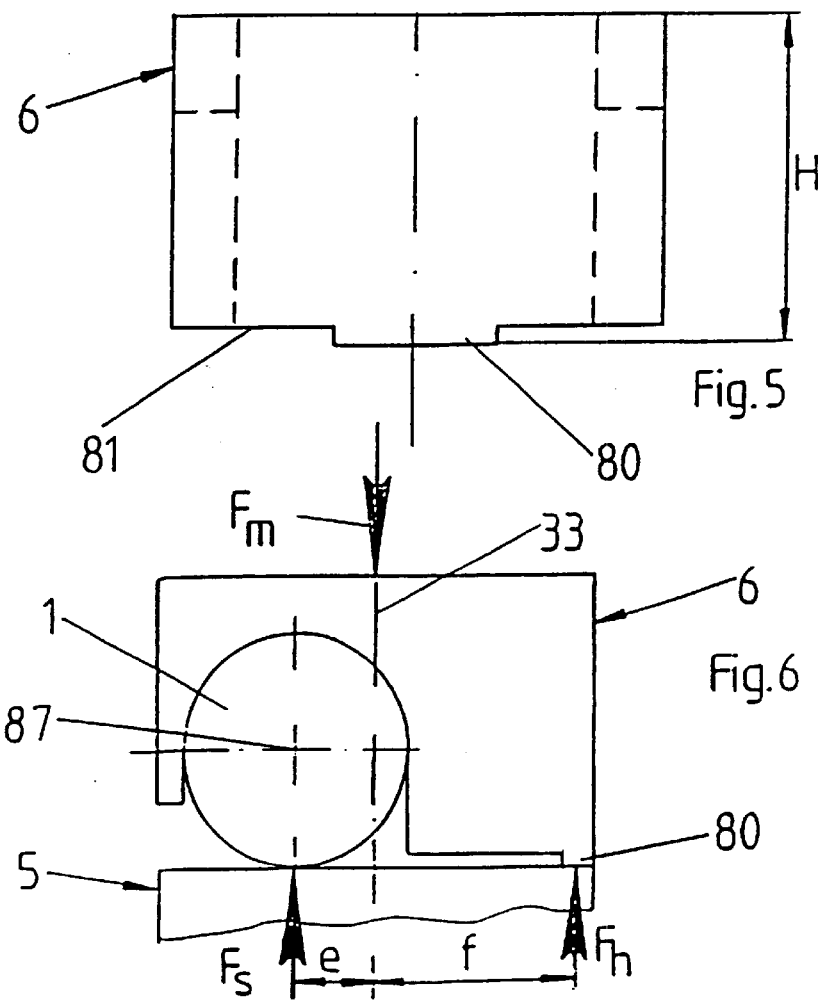
Fig. 5
Fig. 6

DEVICE FOR CONNECTING A LONGITUDINAL SUPPORT TO A BONE ANCHOR

CROSS-REFERENCE TO RELATED APPLICATIONS

This application is a continuation of the U.S. National Phase designation of co-pending International Patent Application No. PCT/CH98/00415, filed Sep. 29, 1998, the content of which is expressly incorporated herein by reference thereto.

FIELD OF THE INVENTION

The present invention relates to spinal fixation systems and, in particular, to a device for connecting a longitudinal support to a bone anchor.

BACKGROUND OF THE INVENTION

Several devices for connecting pedicle screws to longitudinal supports for purposes of vertebral fixation are known in the art. These devices offer the advantage that the individual pedicle screws can be affixed to and removed from the longitudinal support at any time without requiring disassembly of the entire fixation system. In addition, the locked relationship between the head of the pedicle screw and the connection device can be maintained while adjusting the position of the connection device relative to the longitudinal support.

One such connection device is disclosed in U.S. Pat. No. 5,584,834 to Errico et al. The Errico patent discloses a coupling element that provides a simple connection between a pedicle screw and a longitudinal support rod while maintaining considerable angular freedom between the two components. Essentially, the coupling element consists of a generally cylindrical body defining an interior chamber for receiving a head of a screw at its lower portion and an external thread on its upper portion. Slots are formed in the external surface of the lower portion so that the interior chamber may resiliently expand to receive the screw head. The intermediate portion of the cylindrical body includes a side receiving channel for receiving the longitudinal support. A locking collar and a securing sleeve both slide over the cylindrical body and a locking nut is threaded on the external thread of the cylindrical body. The longitudinal support may be inserted through the side receiving channel between the locking collar and the securing sleeve. To lock the coupling element, the locking nut is tightened to provide a downward force on the securing sleeve, longitudinal support rod, and ultimately the locking collar, which compresses the interior chamber and thereby locks the position of the screw.

One disadvantage of the coupling element disclosed in the Errico patent is that the cylindrical body is bent upward when the locking nut is being tightened because of the geometry of the side receiving channel. Consequently, the tightening force applied to the longitudinal support is insufficient and the cylindrical body may elastically deform or the locking collar may warp because of uneven pressure distributed on it. When the cylindrical body bends upward, the longitudinal support tends to slip out of the side receiving channel and consequently the securing sleeve bends up too. This problem can only be solved by fitting the locking collar with a guide groove for partially receiving the longitudinal support. This groove, however, requires aligning the locking collar during assembly and creates a risk of assembly errors.

Moreover, with regard to pressing the locking collar over the lower portion of the cylindrical body to lock the ball-head of the bone screw, there is a risk of warping the lower portion if the surfaces of the lower portion and the locking collar have imprecisely matching surfaces. Also, the geometry of the lower portion may change during tightening of the tightening nut and adversely affect the locking relationship between the coupling element and the ball-head of the screw.

It is therefore desirable to provide a device for connecting a longitudinal support to a bone anchor that distributes locking forces over the device and longitudinal support in a plane perpendicular to a central axis of the locking collar, prevents warping of the cylindrical body and the locking collar, and prevents the longitudinal support from bending upward and slipping out of the side receiving channel.

SUMMARY OF THE INVENTION

The present invention is directed to a device for connecting a longitudinal support to a bone anchor having a rounded head. According to one embodiment, the device includes a body defining a chamber for receiving the rounded head of the bone anchor and a first channel for receiving the longitudinal support. Further, a first sleeve is slidable over the body for compressing the chamber, a second sleeve is slidable over the body for biasing the longitudinal support against the first sleeve at first and second contact points or zones, and a fastener is operatively associated with the body for biasing the second sleeve toward the first sleeve. One of the sleeves includes at least one extended portion for contacting the other sleeve at at least one additional contact point or zone such that forces exerted on the second sleeve by the fastener are transferred to the first sleeve through the at least three contact points or zones. The contact points or zones may be radially displaced about a central axis of the body such that a resultant force exerted by the first sleeve and the longitudinal support on the second sleeve is applied substantially at the central axis.

According to another embodiment, the portion of the body defining the chamber has an outer surface with a convex cross-section. For example, the portion of the body may have a substantially spherical outer surface. Contact between an inner wall of the first sleeve and the outer surface may be along a substantially circular contact zone.

According to yet another embodiment, the body defines an annular recess, and the first sleeve includes a protrusion received in the annular recess. The protrusion limits sliding of the first sleeve on the body such that the chamber cannot expand sufficiently to allow the rounded head of the bone anchor to be removed from the chamber.

BRIEF DESCRIPTION OF THE DRAWINGS

The detailed description will be better understood in conjunction with the accompanying drawings, wherein like reference characters represent like elements, as follows:

FIG. 4 is a bottom view of an upper sleeve of the connecting device of FIG. 1;

FIG. 5 is an elevational view of the upper sleeve of FIG. 4; and

FIG. 6 is a schematic representation of an applied force being distributed over a longitudinal support rod and the upper sleeve of FIG. 4.

DETAILED DESCRIPTION OF THE PREFERRED EMBODIMENTS

Figure 1:
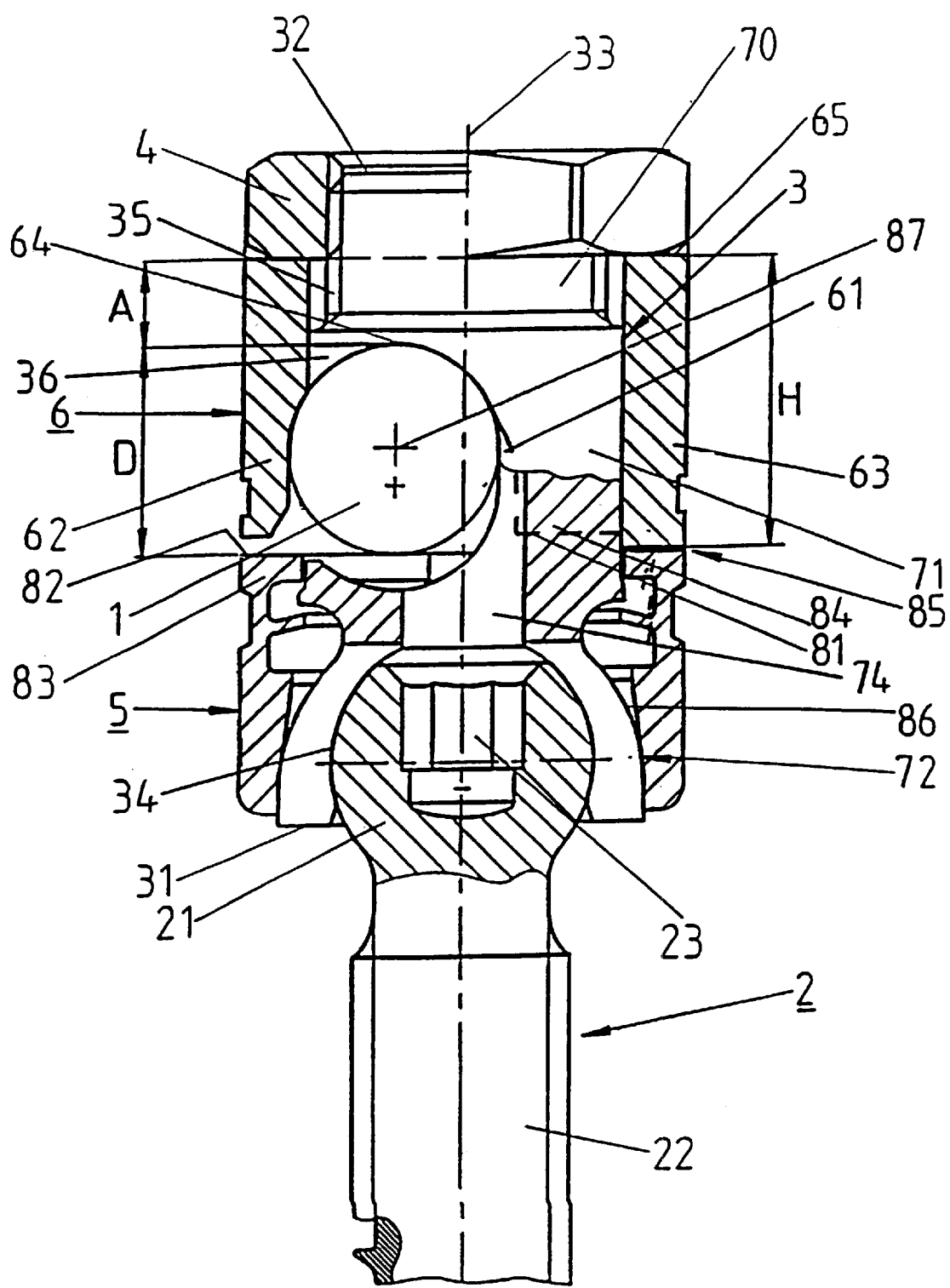
FIG. 1 is a longitudinal cross-section of one preferred embodiment of a connecting device of the present invention shown together with a longitudinal support rod and a bone screw having a ball-head.

Referring to FIG. 1, one embodiment of a connection device according to the present invention includes a body 3 defining a compressible chamber 34, which may receive a ball-shaped head 21 of a bone anchor 2. Chamber 34 is preferably spherical in shape with a downwardly open end, and the exterior surface of lower portion 72 of body 3 defines a substantially convex cross-section in a plane substantially parallel to central axis 33 of body 3. Preferably, exterior surface of lower portion 72 is substantially spherical in the region of chamber 34. The middle portion 71 of body 3, located between the lower chamber 34 and upper portion 70, includes a laterally open first channel 36 for receiving a longitudinal support, shown in FIG. 1 as longitudinal support rod 1. First channel 36 is oriented transversely and eccentrically with respect to the central axis 33 of body 3. An outer thread 35 is formed on an upper portion 70 of body 3.

The connection device further includes a lower sleeve 5 and an upper sleeve 6, both mounted concentrically with body 3, and a tightening nut 4. In order to lock the longitudinal support rod 1 and a ball-head 21 of the bone anchor 2 to the connection device, the tightening nut 4 is threaded on the outer thread 35 and tightened. The upper sleeve 6 defines a downwardly open second channel 61 for receiving the longitudinal support rod 1, which corresponds to the first channel 36 in body 3. Similar to first channel 36, second channel 61 is transverse to the central axis 33 of body 3. Second channel 61 encloses longitudinal support rod 1 from the top and sides, but not from below. Thus, when nut 4 is tightened, upper sleeve 6 is pressed downward and compresses longitudinal support rod 1, inserted in first channel 36 and second channel 61, and longitudinal support rod 1 in turn presses down lower sleeve 5 and slides it downward on lower portion 72 of body 3. As a result, the longitudinal support rod 1 is clamped between the upper and lower sleeves 6, 5, and chamber 34 is compressed over the ball-head 21 of the bone anchor 2, locking its position.

According to one embodiment, second channel 61 divides the upper sleeve 6 into first and second sections 62, 63, which are of different heights. First section 62 serves to block first channel 36 and is of lesser height than diametrically opposed second section 63. The larger height H of second section 63 may be implemented by providing an extended portion 80 projecting from lower surface 81 of upper sleeve 6. As shown in FIG. 4, extended portion 80 extends through an angle β with respect to central axis 33, which is preferably between 5° and about 20°. The height H of second section 63 in the area of extended portion 80 corresponds to the sum H=D+A, where D is the diameter of the longitudinal support rod 1 and A is the distance between the top 64 of second channel 61 and the uppermost surface 65 of upper sleeve 6.

The longitudinal axis 87 of second channel 61 is oriented eccentrically with respect to central axis 33 of body 3 such that first section 62 substantially closes first channel 36 of body 3. Due to the eccentric location of second channel 61, the first section 62 has a smaller cross-section perpendicular to central axis than does diametrically opposed second section 63.

The different heights of first and second sections 62, 63 are dimensioned such that when nut 4 is tightened, only the longitudinal support rod 1 and the extended portion 80 of second section 63 press against lower sleeve 5. Thus, according to this embodiment, the clamping force exerted by nut 4 is distributed to three contact points or zones on lower sleeve 5. The height difference between the first and second sections 62, 63 makes it possible that only the extended portion 80 of second section 63 and the longitudinal support rod 1 press on the lower sleeve 5 when nut 4 is tightened. Because the height H of the second section 63 is equal to the sum D+A, the extended portion 80 and the longitudinal support rod 1 apply uniform pressure to lower sleeve 5 in a plane substantially perpendicular to the central axis 33, as a result of which lower sleeve 5 is maintained coaxially aligned over the spherical outer surface of the body 3 and uniformly compresses chamber 34.

By designing the second section 63 to have an extended portion 80 such that increased height H only extends through angle of about 5° to 20° with respect to central axis 33, it is possible to adjust the distribution of forces along the longitudinal support rod 1 and the surface of extended portion 80. The ratio of force division preferably is 1:3, and accordingly 75% of the compression generated by nut 4 passes through the longitudinal support rod 1 and 25% through the extended portion 80. The clamping of longitudinal support rod 1 is caused by the force transmitted from upper sleeve 6 to lower sleeve 5. The height of lower sleeve 5 may be selected in such a manner that when the longitudinal support rod 1 is inserted through channels 36 and 61, rod 1 cannot contact the bottom of first channel 36 when nut 4 is tightened. Preferably, the height differential between the first and second sections 62, 63 is in the range of 0.3–1.0 mm.

Figure 2:
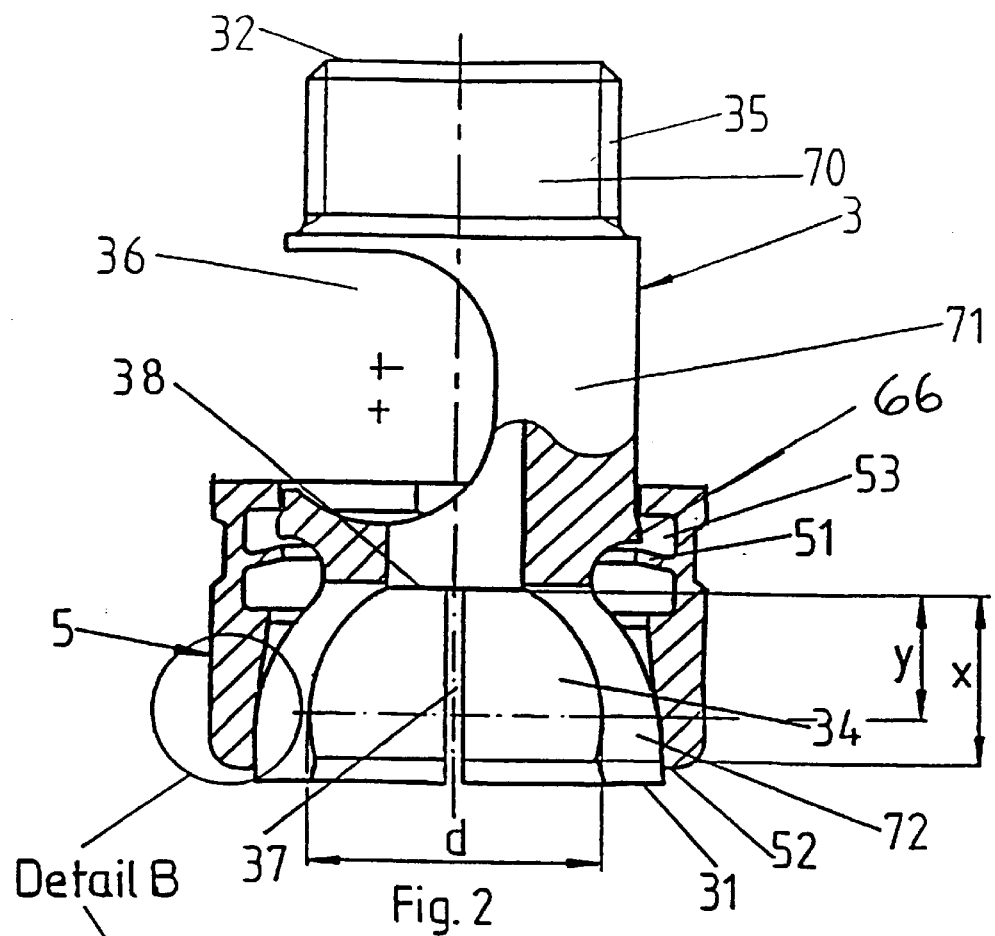
FIG. 2 is a longitudinal cross-section of a body and a lower sleeve of the connecting device of FIG. 1.
Figure 3:
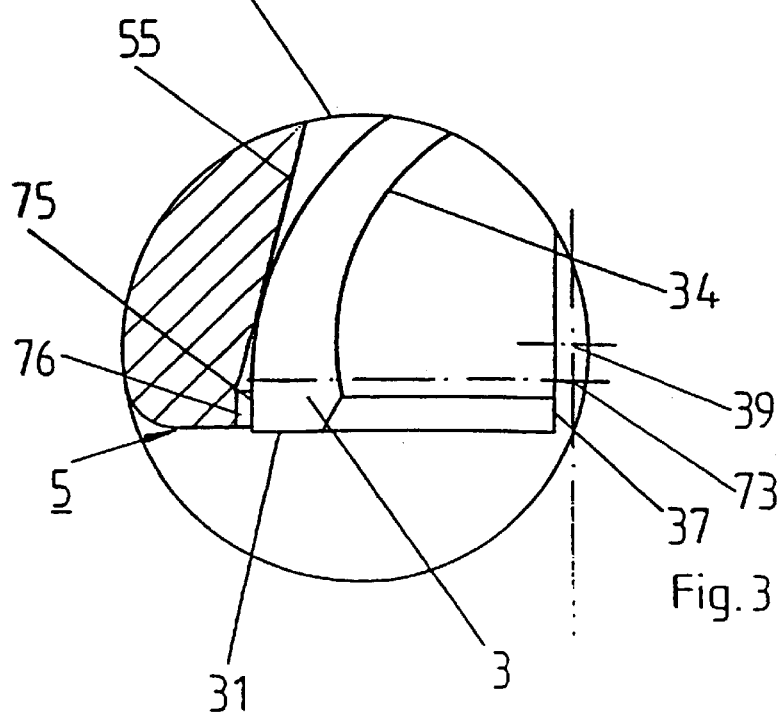
FIG. 3 is an enlarged detail view of a contact zone between the body and the lower sleeve of FIG. 2.

As shown in FIG. 2, chamber 34 has a diameter d and is in the form of a spherical segment of height x, which is preferably less than diameter d. The great-circle plane of the spherical segment perpendicular to central axis 33 is located within chamber 34 at a distance y<x from the top 38 of chamber 34. The exterior surface of lower portion 72 of body 3, in the region of chamber 34, also has a spherical shape. As shown in FIG. 3, the center 73 of shell-like lower portion 72 is located at a point on central axis 33 lower than the center 39 of the spherical segment of chamber 34. Thus, the ball-head 21 of the bone anchor 2 can be resiliently snapped into chamber 34, and is only removable therefrom upon applying a predetermined force. The configuration of chamber 34 allows the shank of a bone anchor 2 that has its ball-head 21 locked in chamber 34 to be locked at a range of angles from about −25° to about 25° relative to the central axis 33. This range of motion substantially increases the applicability and versatility of the connection device of the present invention.

According to one aspect of the present invention, both the ball-head 21 of the bone anchor 2 and the chamber 34 may receive a surface treatment to increase the friction between them. For example, the ball-head 21 and/or the chamber 34 may be knurled or sandblasted. Additionally, the ball-head 21 of the bone anchor 2 may include a section in the treated area of the chamber that is softer than the treated surface of the chamber, or vice versa. This hardness differential may be implemented by differential cold working, differential crystallization of identical materials, or by selecting different materials for the two parts. In the case of different materials, the hard material is preferably high-strained 1.4441 steel or a hard titanium alloy, and the soft material is preferably heat-treated 1.4441 steel or soft pure titanium. The hardness differential may also be implemented by applying a coating or by ion implantation. Corundum blasting of one or both of the contacting parts is also possible. Both the surface treatment and the hardness differential increase the non-rotational locking relationship of the ball-head 21 and chamber 34.

Referring back to FIG. 2, the lower portion 72 of body 3, containing chamber 34, is separated from the middle portion 71 of body 3 by an annular offset 66, and lower sleeve 5 is fitted with projections 51 formed around its inner periphery. The inner diameter of the projections 51 is less than the diameter of the annular offset 66 and, as a result, the lower sleeve 5 may be placed over the upper end 32 of body 3 and the projections 51 resiliently snapped over the annular offset 66. This makes it possible to use lower sleeve 5 as a clamping ring for chamber 34 while being prevented from sliding off of body 3. In this manner, lower sleeve 5 also prevents chamber 34 from expanding sufficiently to allow the ball-head 21 of bone anchor 2 to pop out of chamber 34 when stressed. One of ordinary skill in the art will know and appreciate that projections 51 could alternatively be on the body 3 and that annular offset 66 could be on lower sleeve 5. Further, one of ordinary skill in the art will know and appreciate that neither projections 51 nor annular offset 66 has to be continuous around the circumference of body 3.

According to one aspect of the present invention, the bone anchor 2 may be a pedicle screw. To facilitate turning of the pedicle screw into the bone, the screw may be provided with a hexagonal socket in its ball-head 21. In addition, the body 3 of the connection device may include a continuous bore providing access to the socket in the ball-head 21. This configuration allows the screw to be screwed into the bone independently of the connecting device or in conjunction with the connecting device, providing the advantage of turning-in or turning-out the connecting device at any time to adjust its height.

FIG. 3 is a detail view of the lower portion 72 of body 3, with the outside wall of chamber 34 defining slits 37 open toward the lower end 31 of body 3. Slits 37 allow for the resilient expansion and compression of chamber 34. The lower sleeve 5 acts as a clamping ring and is fitted with a conical inside wall 55 and is slidable over the outside surface of lower portion 72 to compress chamber 34. When lower sleeve 5 is placed over body 3, contact between the spherical outer surface of lower portion 72 and inside wall 55 is tangential to the spherical outer surface of lower portion 72. Thus, contact between lower portion 72 and inside wall 55 is along a circle, defining a circular contact zone. This circular contact zone provides uniform compression of chamber 34 by lower sleeve 5.

Still referring to FIG. 3, lower sleeve 5 has a cylindrical wall section 76 on the inside of its lowermost end, and lower portion 72 has a cylindrical wall section 75 on the outer surface at its lowermost end 31. The diameters, heights and relative positions of the cylindrical walls 75, 76 are matched such that when nut 4 is loosened and lower sleeve 5 slides upward on lower portion 72 until projections 51 engage annular offset 66, cylindrical wall 76 prevents lower portion 72, and ultimately chamber 34, from expanding beyond a predetermined amount and prevents ball-head 21 from popping out of chamber 34.

When manipulating the connecting device and bone anchor 2 in the absence of inserted longitudinal support rod 1 (for instance, when moving the connecting device relative to the longitudinal support rod 1), the play between projections 51 and annular offset 66 only allows the lower sleeve 5 to slide upward on body 3 until cylindrical wall section 76 rests on the outer surface of lower portion 72. This limits the expansion of lower portion 72 and chamber 34 and reduces the chances of ball-head 21 snapping out of chamber 34 when force is exerted on the bone anchor 2.

FIGS. 4 and 5 show the upper sleeve 6 and second channel 61 extending eccentrically with respect to central axis 33, and the extended portion 80 projecting from the lower section 81. Extended portion 80 has a height H, which extends through angle β, shown in FIG. 4.

FIG. 6 shows the resulting forces acting on longitudinal support rod 1 and on upper sleeve 6 when nut 4 (not shown) is tightened. As shown therein, $F_M$ schematically represents the resulting force exerted by nut 4, $F_S$ schematically represents the resulting force exerted by lower sleeve 5 on the longitudinal support rod 1, and $F_H$ schematically represents the resulting force exerted by the lower sleeve 5 on the extended portion 80. As also shown in FIG. 6, a distance e is subtended on the diameter of upper sleeve 6 perpendicular to the longitudinal axis 87 of second channel 61 between the application point of resulting force $F_S$ and the central axis 33, and a distance f is subtended on the diameter perpendicular to longitudinal axis 87 between the application point of the resultant force $F_H$ and the central axis 33. The distance e also corresponds to the distance between the longitudinal axis 87 of second channel 61 and the central axis 33. Based on equilibrium of forces and torques, $F_S=F_M/[1+e/f]$. For a ratio e/f of ⅓, which follows from designing an upper sleeve 6 with dimensions e=2 mm and f=6 mm, the ratio of $F_S/F_M$=0.75.

The connection described above provides numerous advantages over the prior art. Due to the precise tangential contact between the inside wall 55 of lower sleeve 5 and the spherical outer surface of lower portion 72, lower sleeve 5 provides a uniform clamping force on lower portion 72, which in turn provides uniform clamping force between chamber 34 and ball-head 21. In addition, the height difference between the first and second sections 62, 63 makes it possible to distribute the force exerted by nut 4 over longitudinal support rod 1 and extended portion 80, thus transmitting this force to three or more contact points or zones on lower sleeve 5. This assures that lower sleeve 5 remains accurately and coaxially aligned on body 3 when forced is applied by nut 4. Furthermore, projections 51 on the inner periphery of the lower sleeve 5 and the corresponding annular offset 66 of the body 3 make it possible to have lower sleeve 5 slidable on body 3 while being prevented from sliding off the top of body 3. Projections 51 thus prevent lower sleeve 5 from sliding upward far enough on body 3 for lower portion 72 to expand sufficiently to release ball-head 21 from chamber 34. As a result, a larger amount of force may be applied from the connecting device to the spinal column without the possibility of body 3 unintentionally detaching from the ball-head 21.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed:

1. A device for connecting a longitudinal support to a bone anchor having a rounded head comprising:
   a body defining a central axis and having a chamber for receiving the rounded head of the bone anchor and a first channel for receiving the longitudinal support;
   a first sleeve at least partially slidable over the body for compressing the chamber;
   a second sleeve at least partially slidable over the body for biasing the longitudinal support against the first sleeve at first and second contact zones; and
   a fastener operatively associated with the body for biasing the second sleeve toward the first sleeve;
   wherein one of the sleeves includes at least one extended portion for contacting the other sleeve at at least one additional contact zone such that forces exerted on the second sleeve by the fastener are transferred to the first sleeve through at least three contact zones.

2. The device of claim 1, wherein the at least three contact zones are radially displaced about the central axis such that a resultant force exerted by the second sleeve and the longitudinal support on the first sleeve is applied substantially at the central axis.

3. The device of claim 1, wherein the second sleeve includes a second channel open generally transversely to the first channel to lock the longitudinal support in the first channel.

4. The device of claim 3, wherein the second channel defines a longitudinal axis that is laterally offset with respect to the central axis.

5. The device of claim 3, wherein:
   the second channel divides the second sleeve into a first section and second section having a greater height than the first section; and
   the extended portion comprises the second section;
   wherein when the first sleeve is biased against the second sleeve the second section contacts the second sleeve, and the first section is prevented from contacting the second sleeve.

6. The device of claim 3, wherein the second channel divides the second sleeve into first and second sections, and the extended portion is disposed on one of the sections and extends through an angle of about 5° to about 20° with respect to the central axis.

7. The device of claim 6, wherein the extended portion is disposed on the first section and is diametrically opposed with respect to the second section about the central axis.

8. The device of claim 1, wherein the body includes a first portion with the chamber defined therein and a second portion with the first channel defined therein, and the first portion has an at least partially spherical outer surface.

9. The device of claim 1, wherein sliding of the first sleeve on the body along the central axis is limited.

10. The device of claim 9, wherein one of the body and first sleeve defines an annular recess in a plane substantially transverse to the central axis, and the other defines a protrusion received in the annular recess.

11. The device of claim 1, wherein the first channel defines a longitudinal axis that is laterally offset with respect to the central axis.

12. A device for connecting a longitudinal support to a bone anchor having a rounded head comprising:
   a body defining a central axis of the device and including:
      a first portion defining a chamber for receiving the rounded head of the bone anchor and having an outer surface with a convex cross-section in a plane substantially parallel to the central axis; and
      a second portion defining a channel for receiving the longitudinal support; and
   a first sleeve at least partially slidable over the body for compressing the first portion;
   a second sleeve at least partially slidable over the body for locking the longitudinal support in the channel; and
   a fastener operatively associated with the body for retaining at least one of the sleeves.

13. The device of claim 12, wherein the outer surface of the first portion is at least partially spherical.

14. The device of claim 12, wherein the first sleeve includes a generally conical inner wall, and contact between the inner wall and the outer surface of the first portion is substantially tangential to the outer surface.

15. The device of claim 12, wherein the first sleeve includes a generally conical inner wall, and contact between the inner wall and the outer surface of the first portion is along a substantially circular contact zone.

16. The device of claim 12, wherein:
   the outer surface of the first portion has a first center point;
   the rounded head of the bone anchor has a second center point; and
   the first center point is offset from the second center point along the central axis.

17. The device of claim 12, wherein sliding of the first sleeve on the body is limited such that the first sleeve is prevented from sliding off of the first portion and prevents the chamber from expanding sufficiently to allow the rounded head of the bone anchor from being removed from the chamber.

18. The device of claim 17, wherein one of the the body and the first sleeve is configured and dimensioned to have at least one annular recess in a plane substantially transverse to the central axis; and
   the other of the first sleeve and body has at least one protrusion, wherein the at least one protrusion is configured and dimensioned to be received in the annular recess.

19. The device of claim 12, wherein:
   the longitudinal support contacts the second sleeve at first and second contact zones; and
   one of the sleeves includes at least one extended portion for contacting the other sleeve at at least one additional contact zone such that forces exerted on the second sleeve by the fastener are transferred to the first sleeve through at least three contact zones.

20. A device for connecting a longitudinal support to a bone anchor having a rounded head comprising:
   a body defining a central axis of the device and including a first portion defining a chamber for receiving the rounded head of the bone anchor and a second portion defining a channel for receiving the longitudinal support;
   a first sleeve at least partially audible over the body for compressing the chamber;
   a second sleeve at least partially slidable over the body for locking the longitudinal support in the channel; and
   a fastener operatively associated with the body for retaining at least one of the sleeves;
   wherein sliding of the first sleeve from the first portion of the body toward the second portion of the body is limited sufficiently to prevent the chamber from expanding sufficiently to allow the rounded head of the bone anchor from being removed from the chamber.

21. The device of claim 20, wherein one of the body and the first sleeve defines at least one annular recess substantially perpendicular to the central axis and the other one of the body and the first sleeve defines at least one protrusion configured to be received in the annular recess.

22. The device of claim 21, wherein the first sleeve defines an inner wall for contacting an outer surface of the first portion of the body and the inner wall is maintained in contact with the outer surface.

23. The device of claim 20 wherein the first portion has an at least partially spherical outer surface.

24. The device of claim 23, wherein the first sleeve includes a generally conical inner wall, and contact between the inner wall and the outer surface of the first portion is substantially tangential to the outer surface.

25. The device of claim 23, wherein the first sleeve includes a generally conical inner wall, and contact between the inner wall and the outer surface of the first portion is along a substantially circular contact zone.

26. The device of claim 20, wherein:
   the longitudinal support contacts the second sleeve at first and second contact zones; and
   one of the sleeves includes at least one extended portion for contacting the other sleeve at at least one additional contact zone such that forces exerted on the second sleeve by the fastener are transferred to the first sleeve through at least three contact zones.

27. The device of claim 26, wherein the at least three contact zones are radially displaced about the central axis such that a resultant force exerted by the second sleeve and the longitudinal support on the first sleeve is applied substantially at the central axis.

28. The device of claim 26, wherein the second sleeve includes a second channel open generally transversely to the channel to lock the longitudinal support in the channel.

29. The device of claim 28, wherein the second channel defines a longitudinal axis that is laterally offset with respect to the central axis.

30. The device of claim 28, wherein:
   the second channel divides the second sleeve into a first section and second section having a greater height than the first section; and
   the extended portion comprises the second section;
   wherein when the first sleeve is biased against the second sleeve the second section contacts the second sleeve, and the first section is prevented from contacting the second sleeve.

31. The device of claim 20, wherein the channel defines a longitudinal axis that is laterally offset with respect to the central axis.

* * * * *